United States Patent
Yu et al.

(10) Patent No.: US 10,901,195 B2
(45) Date of Patent: Jan. 26, 2021

(54) RECONFIGURABLE SURGICAL MICROSCOPE

(71) Applicant: Novartis AG, Basel (CH)

(72) Inventors: Lingfeng Yu, Rancho Santa Margarita, CA (US); Craig Bender, Laguna Niguel, CA (US)

(73) Assignee: Alcon Inc.

( * ) Notice: Subject to any disclaimer, the term of this patent is extended or adjusted under 35 U.S.C. 154(b) by 74 days.

(21) Appl. No.: 15/924,786

(22) Filed: Mar. 19, 2018

(65) Prior Publication Data

US 2018/0275386 A1    Sep. 27, 2018

Related U.S. Application Data

(60) Provisional application No. 62/474,916, filed on Mar. 22, 2017.

(51) Int. Cl.
*G02B 21/00* (2006.01)
*G02B 21/02* (2006.01)
(Continued)

(52) U.S. Cl.
CPC ............ *G02B 21/025* (2013.01); *A61B 3/13* (2013.01); *A61F 9/007* (2013.01);
(Continued)

(58) Field of Classification Search
CPC ............... G02B 21/00; G02B 21/0008; G02B 21/0012; G02B 21/0016; G02B 21/0032;
(Continued)

(56) References Cited

U.S. PATENT DOCUMENTS

| 4,337,991 A | * | 7/1982 | Benajam | G02B 21/24 359/391 |
| 5,270,855 A | * | 12/1993 | Hasegawa | G02B 21/26 359/368 |

(Continued)

FOREIGN PATENT DOCUMENTS

| EP | 1447698 B1 | 4/2007 |
| JP | 2005242386 A | 9/2005 |
| JP | 2007025212 A | 2/2007 |

OTHER PUBLICATIONS

An English abstract of the Japanese reference No. 2009-297093 published on Dec. 24, 2009.*
(Continued)

*Primary Examiner* — Thong Q Nguyen
(74) *Attorney, Agent, or Firm* — Joseph Weatherbee, Esq.

(57) ABSTRACT

A system and method for a reconfigurable surgical microscope is disclosed. The reconfigurable microscope includes an eyepiece; a relay lens system optically coupled to the eyepiece; a zoom lens system optically coupled to the eyepiece and the relay lens system; an illumination unit; and an objective lens capable of being repositioned between a first objective lens position and a second objective lens position, the first objective lens position comprising a slot located between the zoom lens system and the illumination unit and the second objective lens position comprising a slot located such that the illumination unit is located between the second objective lens position and the zoom lens system.

4 Claims, 5 Drawing Sheets

(51) Int. Cl.
  *A61B 3/13* (2006.01)
  *A61F 9/007* (2006.01)
  *G02B 21/06* (2006.01)
  *G02B 21/24* (2006.01)
  *A61B 90/20* (2016.01)
  *A61B 90/30* (2016.01)

(52) U.S. Cl.
  CPC ......... *G02B 21/0012* (2013.01); *G02B 21/06* (2013.01); *G02B 21/248* (2013.01); *A61B 90/20* (2016.02); *A61B 90/30* (2016.02)

(58) Field of Classification Search
  CPC ...... G02B 21/02; G02B 21/025; G02B 21/06; G02B 21/24; G02B 21/248; G02B 7/00; G02B 7/003; G02B 7/02; G02B 7/023
  See application file for complete search history.

(56) References Cited

U.S. PATENT DOCUMENTS

| | | | |
|---|---|---|---|
| 5,801,807 A * | 9/1998 | Satake | A61B 3/13 351/214 |
| 7,907,336 B2 * | 3/2011 | Abele | A61B 3/13 359/385 |
| 2001/0003490 A1 * | 6/2001 | Kawasaki | G02B 21/06 359/385 |
| 2003/0201378 A1 * | 10/2003 | Ishikawa | G02B 7/04 250/201.3 |
| 2006/0098274 A1 * | 5/2006 | Kitajima | A61B 3/132 359/385 |
| 2008/0058734 A1 | 3/2008 | Hanft | |
| 2012/0057226 A1 | 3/2012 | Kuster | |
| 2012/0140173 A1 * | 6/2012 | Uhlhorn | A61B 3/1225 351/206 |
| 2017/0042419 A1 * | 2/2017 | Nakanishi | A61F 9/007 |

OTHER PUBLICATIONS

An English abstract of the Japanese reference No. 2011-110172 published on Jun. 9, 2011.*

An English abstract of the WO No. 2008/076777 published on Jun. 26, 2008.*

* cited by examiner

RECONFIGURABLE SURGICAL MICROSCOPE

TECHNICAL FIELD

The present invention generally relates to optical microscopes and, in particular, to systems and methods for a reconfigurable surgical microscope.

BACKGROUND

Optical microscopes are used in a variety of applications to provide the user with an enlarged picture of a specimen in the field of view of the microscope. For example, microscopes may be used in surgical, laboratory, and quality assurance applications. Optical microscopes use visible light and a system of lenses to magnify the specimen.

One type of optical microscope is a common main objective microscope. Common main objective microscopes use a single common main objective lens that is shared between a pair of eyepieces and a lens system. Based on the placement of the objective lens within the microscope, these microscopes offer various depths of focus, lateral resolutions and depth perceptions to a user.

SUMMARY OF THE INVENTION

In accordance with some embodiments of the present disclosure, a reconfigurable surgical microscope is disclosed. The reconfigurable surgical microscope includes an eyepiece; a relay lens system optically coupled to the eyepiece; a zoom lens system optically coupled to the eyepiece and the relay lens system; an illumination unit; and an objective lens capable of being repositioned between a first objective lens position and a second objective lens position. The first objective lens position includes a slot located between the zoom lens system and the illumination unit and the second objective lens position includes a slot located such that the illumination unit is located between the second objective lens position and the zoom lens system.

In accordance with another embodiment of the present disclosure, an automated surgical microscope configuration system is disclosed. The automated surgical microscope configuration system includes a processor; a position sensor coupled to the processor; a reconfigurable surgical microscope coupled to the position sensor. The reconfigurable surgical microscope includes a reconfigurable objective lens capable of being repositioned between a first objective lens position and a second objective lens position. The first objective lens position includes a slot located between the zoom lens system and the illumination unit and the second objective lens position includes a slot located such that the illumination unit is located between the second objective lens position and the zoom lens system. The automated surgical microscope also includes an actuator coupled to the processor and the reconfigurable objective lens and configured to move the reconfigurable objective lens into either the first lens position or the second lens position.

In accordance with a further embodiment of the present disclosure, a method for configuring a reconfigurable surgical microscope is disclosed. The method for configuring a reconfigurable surgical microscope includes determining an initial configuration of the reconfigurable surgical microscope, the reconfigurable surgical microscope including a reconfigurable objective lens; and initiating a reconfiguration process. The reconfiguration process includes removing the reconfigurable objective lens from an initial position corresponding to the initial configuration; and positioning the reconfigurable objective lens into a second position within the reconfigurable surgical microscope.

BRIEF DESCRIPTION OF THE DRAWING

For a more complete understanding of the present disclosure and its features and advantages, reference is now made to the following description, taken in conjunction with the accompanying drawings, in which:

FIG. 2A shows an example of a reconfigurable objective lens with a structural profile that ensures that reconfigurable objective lens is properly positioned within either first slot or second slot;

FIG. 2B shows an alternative profile for the opto-mechanical housing and slots where tabs are T-shaped; and FIG. 2C shows an alternative profile for the opto-mechanical housing and slots where tabs are angle-shaped;

DETAILED DESCRIPTION

The present disclosure provides a common main objective lens microscope that is reconfigurable such that a single microscope may provide optimized optical performance for various applications. The common main objective lens microscope may also include an automation system to allow for automatic switching between configurations.

A further description of the embodiments of the common main objective lens microscope, components thereof, and methods of its uses is presented with reference to FIGS. 1A through 4.

Figure 1A:
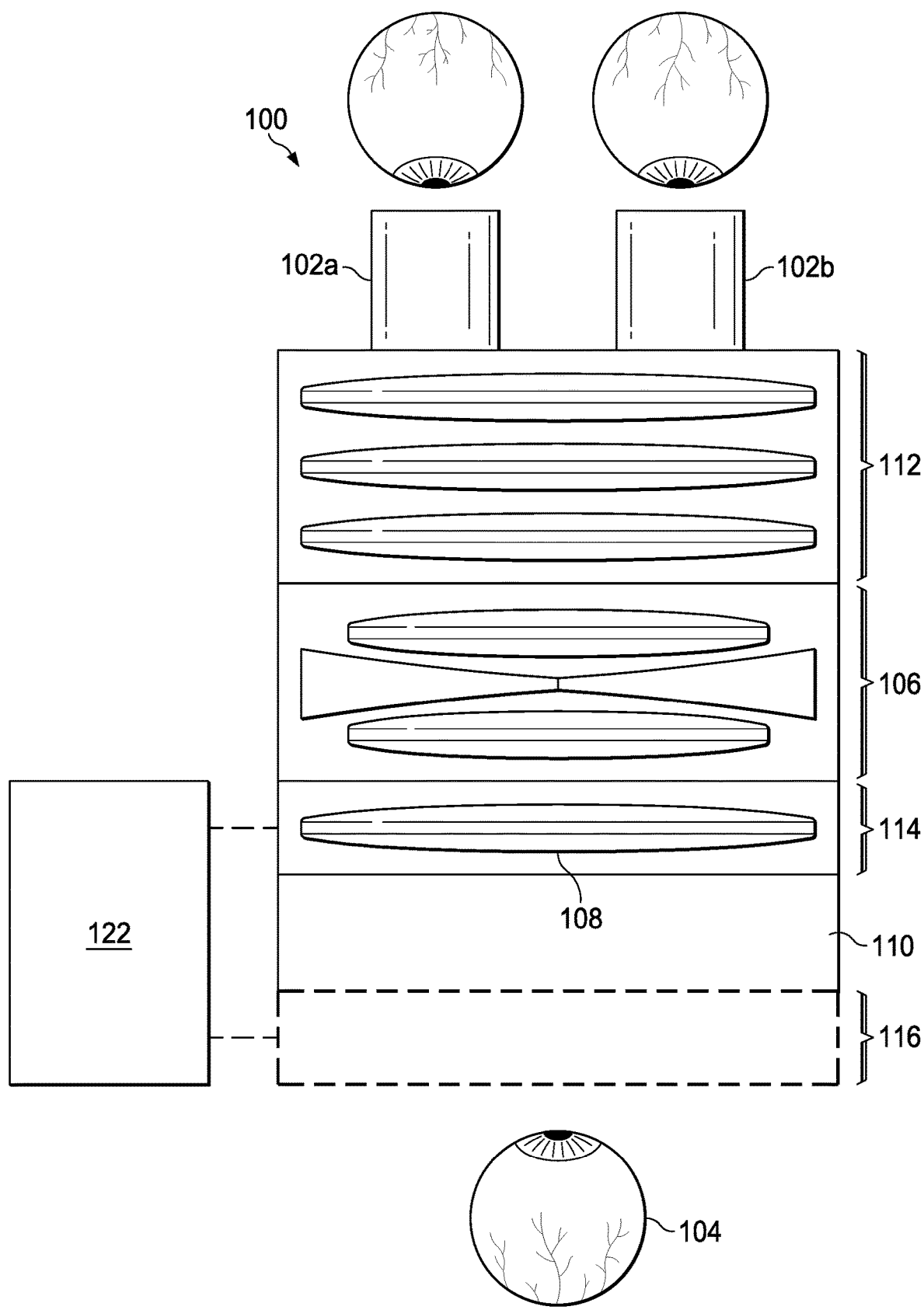
FIG. 1A is a schematic view of a reconfigurable surgical microscope configured in "Cataract Mode;"

FIG. 1A is a schematic view of a reconfigurable surgical microscope configured in "Cataract Mode." Microscope 100 includes eyepieces 102a and 102b. The user of the microscope views a magnified image of the specimen 104 through eyepieces 102a, 102b. Specimen 104 is shown in FIG. 1A as an eye, but may be any specimen viewed using microscope 100. Eyepieces 102a and 102b may also be replaced with other components that provide a stereoscopic view of specimen 104, such as two digital displays.

The image of specimen 104 is magnified through the zoom lens system 106, reconfigurable objective lens 108, and relay lens system 112. Illumination unit 110 illuminates specimen 104. Illumination unit 110 may be configured to provide various types of illumination depending on the application for which the reconfigurable surgical microscope is being used. For example, illumination unit 110 may provide illumination of various brightness, intensity, and area. When illuminated by illumination unit 110, specimen 104 reflects light. Reconfigurable objective lens 108 collects the reflected light from specimen 104. Zoom lens system 106 may include one or more lenses that may move relative to one another to increase or decrease the magnification of the image of specimen 104 that appears at eyepieces 102a, 102b. Zoom lens system 106 divides the image of specimen 104 into a stereo view. Relay lens system 112 further magnifies the image and provides an image to the user through eyepieces 102a, 102b.

As shown in FIG. 1A, reconfigurable objective lens 108 is located in a first slot 114 located below zoom lens system 106 and above illumination unit 110. In this configuration, reconfigurable objective lens 108 may have a focal length that is longer than the specified working distance of reconfigurable objective lens 108. The specified working distance may indicate the distance between the specimen and the lens of the microscope. For example, reconfigurable objective lens 108 may be specified for a 225 mm working distance, 200 mm working distance, a 175 mm working distance, or a 150 mm working distance. The reconfigurable objective lens 108 may also be specified for other working distances. Also for example, the actual focal length of reconfigurable objective lens 108 may be 50 mm, 60 mm, or 70 mm longer than the specified working distance of reconfigurable objective lens 108. The actual focal length of reconfigurable objective lens 108 may also vary by other distances. The discrepancy between the actual focal length and the specified working distance of reconfigurable objective lens 108 may be to accommodate for the width of illumination unit 110. The longer focal length of reconfigurable objective lens 108 may decrease the lateral resolution of microscope 100 and increase the depth of focus. For example, the lateral resolution may be decreased by 10%, 15%, 20%, 25%, or 30%. The lateral resolution may also be decreased by more or less than the stated examples. An increased depth of focus may be desirable in some applications, e.g., cataract surgery. Reconfigurable surgical microscope 100 may also be configured such that reconfigurable objective lens 108 may also be located in a second slot 116 located below illumination unit 110 and above specimen 104. As shown in FIG. 1A, second slot does not contain reconfigurable objective lens 108 or any other structure. When reconfigurable objective lens 108 is located in the first slot 114 as shown in FIG. 1A, microscope 100 may be said to be operating in "Cataract Mode."

Figure 1B:
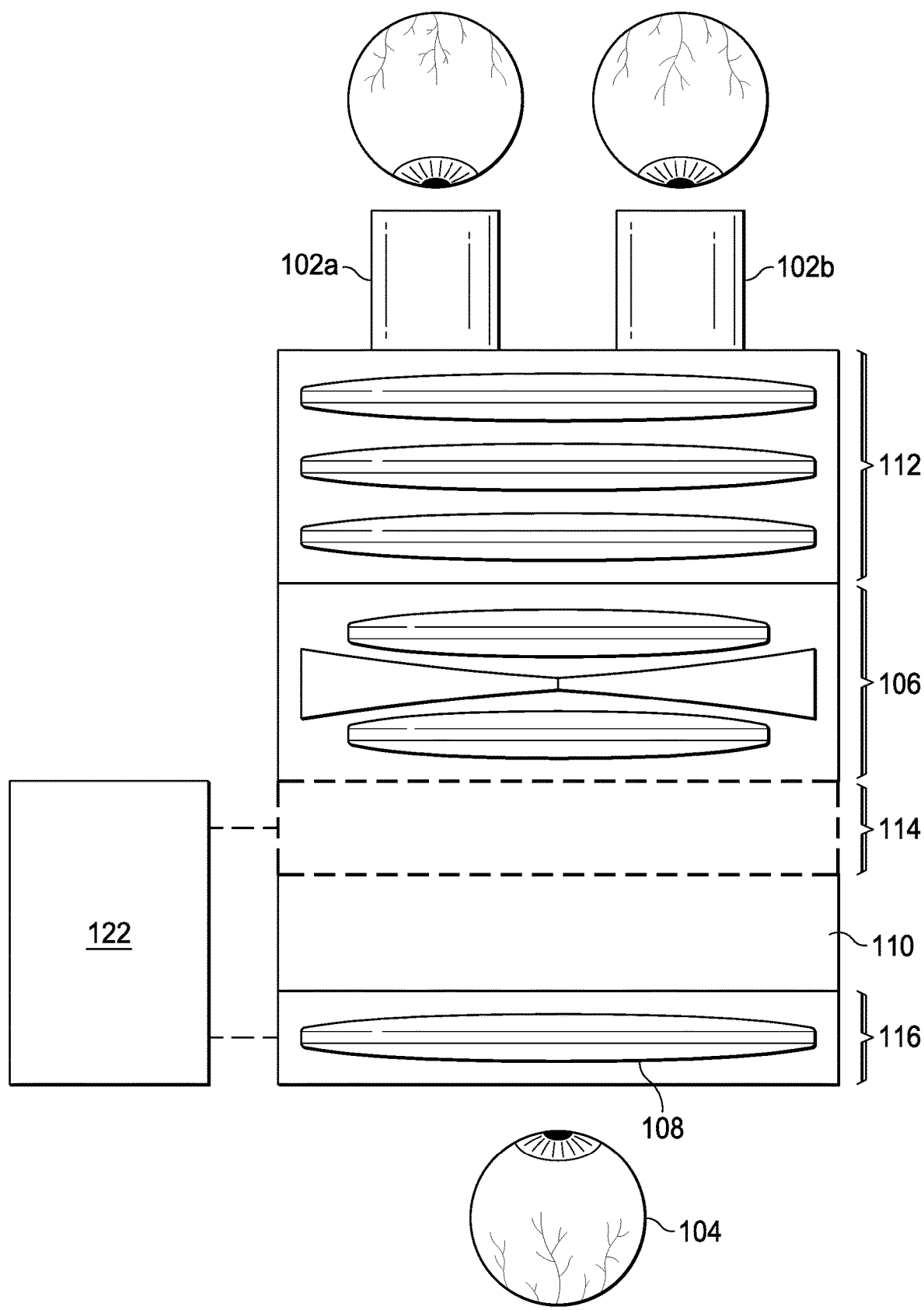
FIG. 1B is a schematic view of a reconfigurable surgical microscope configured in "Vitreoretinal Mode;"

FIG. 1B is a schematic view of a reconfigurable surgical microscope configured in "Vitreoretinal Mode." Microscope 100 of FIG. 1B is the same microscope 100 of FIG. 1A in a different configuration. As shown in FIG. 1B, reconfigurable objective lens 108 is located in second slot 116 located below illumination unit 110 and above specimen 104. In this configuration, reconfigurable objective lens 108 may not have a focal length that is longer than the specified working distance of reconfigurable objective lens 108. For example, reconfigurable objective lens 108 may be specified for a 225 mm working distance, 200 mm working distance, a 175 mm working distance, or a 150 mm working distance. The reconfigurable objective lens 108 may also be specified for other working distances. The actual focal length of reconfigurable objective lens 108 may be approximately equivalent to the specified working distance of reconfigurable objective lens 108. In this configuration, the user of microscope 100 may experience optimal lateral resolution and sharper depth perception. This configuration may be desirable in some applications. For example, vitreoretinal surgeons may desire the increased depth perception and decreased depth of focus as a safeguard to guide the surgical manipulation. Reconfigurable surgical microscope 100 may also be configured such that reconfigurable objective lens 108 may also be located in first slot 114 below zoom lens system 106 and above illumination unit 110. As shown in FIG. 1B, first slot 114 does not contain reconfigurable objective lens 108 or any other structure. When reconfigurable objective lens 108 is positioned as shown in FIG. 1B, microscope 100 may be said to be operating in "Vitreoretinal Mode."

Microscope 100 may be configured in either the Cataract Mode or the Vitreoretinal mode based on the application for which microscope 100 is currently being used. A user of microscope 100 may manually configure microscope 100 by removing and repositioning reconfigurable objective lens 108. Reconfigurable objective lens 108 may be enclosed in a opto-mechanical housing. This housing may prevent damage to reconfigurable objective lens 108 and make for easier handling of reconfigurable objective lens 108 by the user. The opto-mechanical housing of reconfigurable objective lens 108 may be structured to ensure that reconfigurable objective lens 108 is positioned correctly within either first slot 114 or second slot 116, as shown in more detail in FIGS. 2A to 2C.

Figure 2A:
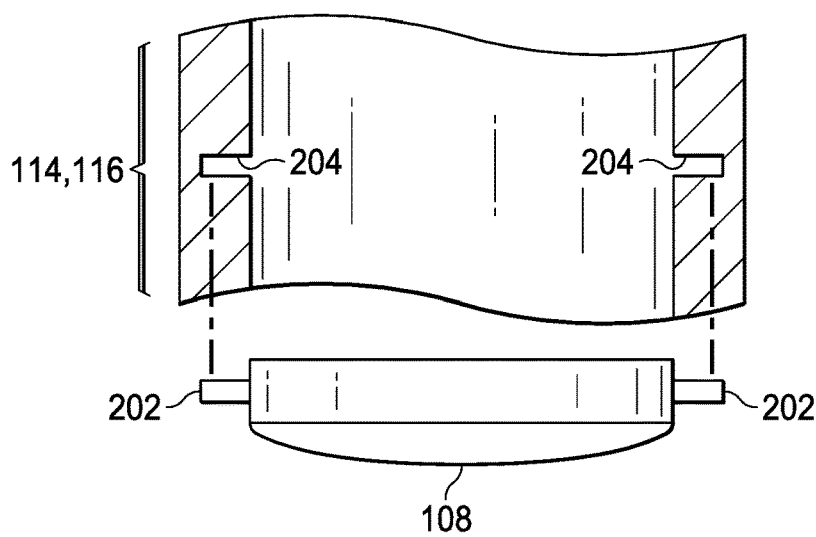
FIGS. 2A to 2C are diagrams of reconfigurable objective lens profiles and reconfigurable microscope slots for a reconfigurable microscope shown in FIGS. 1A and 1B.
Figure 2B:
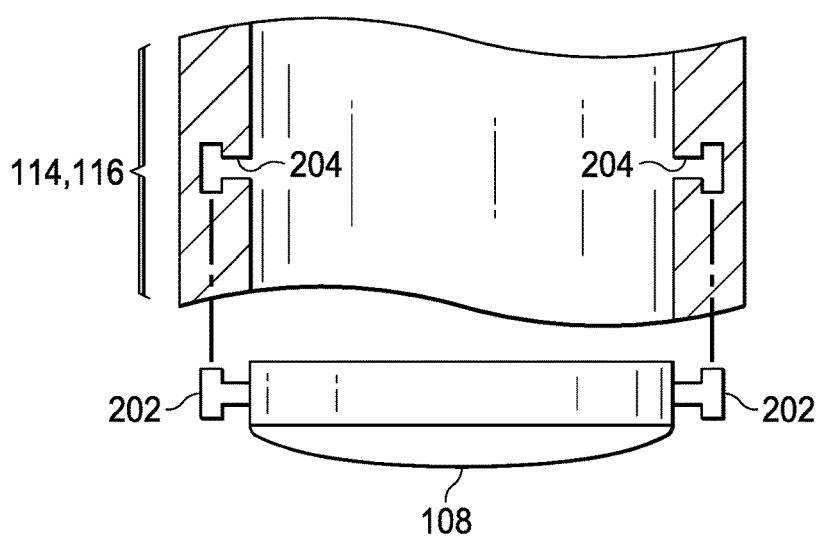
Figure 2C:
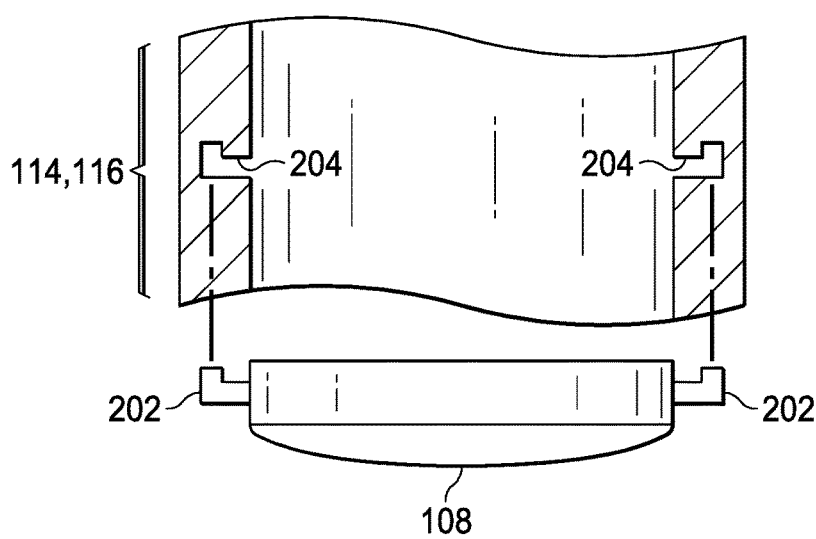

FIGS. 2A to 2C are diagrams of reconfigurable objective lens profiles and reconfigurable microscope slots. FIG. 2A shows an example of a reconfigurable objective lens 108 with a structural profile that ensures that reconfigurable objective lens 108 will be properly positioned within either first slot 114 or second slot 116. As shown in FIG. 2A, reconfigurable objective lens 108 is enclosed in an opto-mechanical housing that has a profile that includes tabs 202. Tabs 202 may be formed along the entire edge of the opto-mechanical housing of reconfigurable objective lens 108 or may have a length shorter than that of the opto-mechanical housing of reconfigurable objective lens 108. As also shown in FIG. 2A, first slot 114 and/or second slot 116 may also be modified to include recesses 204 that are designed to have tabs 202 inserted within them when reconfigurable objective lens 108 is positioned in either first slot 114 or second slot 116. FIG. 2B shows an alternative profile for the opto-mechanical housing and slots where tabs 202 are T-shaped, FIG. 2C shows an alternative profile for the opto-mechanical housing and slots where tabs 202 are angle-shaped. Tabs 202 and the recesses within first slot 114 and second slot 116 may be modified to have any other suitable profile that ensures reconfigurable objective lens 108 is properly positioned within first slot 114 and/or second slot 116.

When microscope 100 is being configured in Cataract Mode, a first reconfigurable objective lens 108 may be used. When microscope 100 is being configured in Vitreoretinal Mode, the same reconfigurable objective lens 108 that was used in Cataract Mode may be used or a second reconfigurable objective lens 108 may be used. The user may desire different optical characteristics of reconfigurable objective lens 108 based on the application of microscope 100. Thus various reconfigurable objective lenses 108 may be used to achieve the desired optical performance.

Figure 3:
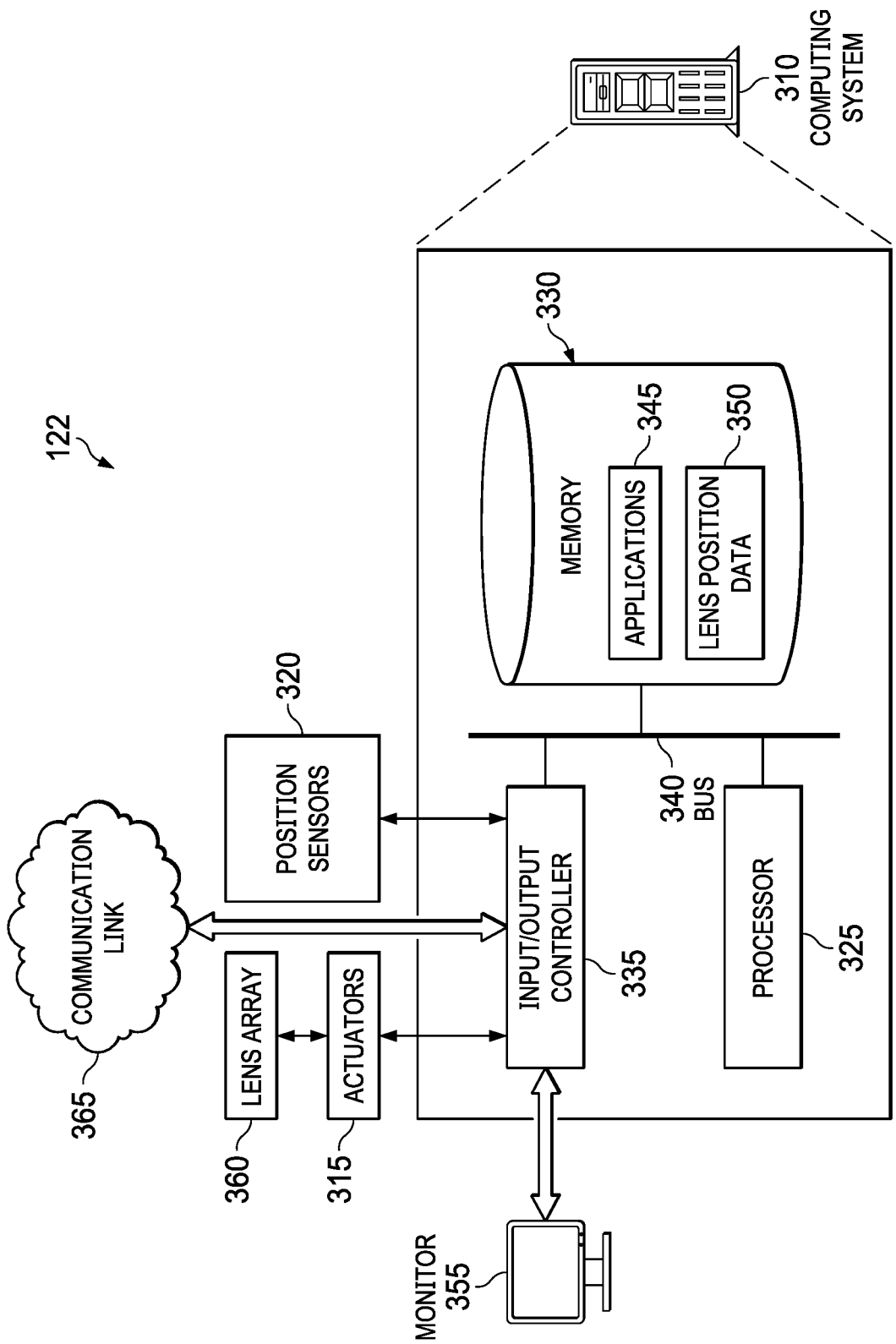
FIG. 3 is a block diagram of an automated surgical microscope configuration system for a reconfigurable surgical microscope system shown in FIGS. 1A and 1B.

Microscope 100 may additionally include automated surgical microscope configuration system 122, as shown in more detail in FIG. 3. Automated surgical microscope configuration system 122 may include one or more actuators 315, one or more position sensors 320, and processor 325. Actuators 315 may configure the microscope into and out of the desired configuration, e.g., either Cataract Mode or Vitreoretinal Mode. Position sensors 320 may be located on the body of microscope 100 to allow position sensors 320 to detect the presence and positions of reconfigurable objective lenses 108 as reconfigurable objective lenses 108 are removed and positioned in either a Cataract Mode configuration or a Vitreoretinal Mode configuration. Processor 325 may execute a software program that determines when reconfigurable objective lenses 108 have been fully removed, and fully repositioned such that microscope 100 has been fully reconfigured from Cataract Mode to Vitreoretinal Mode or from Vitreoretinal Mode to Cataract Mode. Once processor 325 determines that the reconfiguration process has been completed, processor 325 may send a command to actuators 315 to stop repositioning reconfigurable objective lenses 108 and may indicate that reconfiguration is complete to the user.

FIG. 3 is a block diagram of an automated surgical microscope configuration system for the reconfigurable microscope system shown in FIGS. 1A and 1B. Automated surgical microscope configuration system 122 may include computing subsystem 310, actuators 315, position sensors 320, monitor 355, lens array 360, and communication link 365. Actuators 315 may be coupled to a movable objective lens in a reconfigurable microscope system 100, such as reconfigurable objective lens 108 in FIG. 1A or FIG. 1B. Actuators 315 may include one or more actuators. If a single actuator 315 is used, this actuator may be configured such that this acutuator is coupled to multiple reconfigurable objective lenses 108 and may be capable of positioning reconfigurable objective lenses 108 into and out of either the first position or second position as shown in FIG. 1A and FIG. 1B. Actuators 315 may be activated to change the position of the reconfigurable objective lens and thus change the configuration of the reconfigurable microscope system. Actuators 315 may be any suitable type of actuator including a stepper motor, an electric motor, a servomotor, a rotary actuator, a liner actuator, or any combination thereof. The position of the movable lens may be recorded in lens position data 350, discussed in further detail below.

Position sensors 320 may sense the position of a reconfigurable objective lens, such as reconfigurable objective lens 108 shown in FIGS. 1A and 1B, within reconfigurable microscope 100. For example, the position may include whether an reconfigurable objective lens is positioned in a first position or a second position. This position data may also include whether the reconfigurable objective lens is aligned within the desired position such that the lens does not interfere with the functionality of the reconfigurable microscope. For example, the position data may indicate whether the reconfigurable objective lens is interfering with the field of view of the reconfigurable microscope or whether the reconfigurable objective lens is interfering with the illumination unit when the objective lens is located in the second position or in "Vitreoretinal Mode."

Position sensor 320 may then transmit the position to computing subsystem 310 for storage as lens position data 350 as discussed in further detail below. Position sensors 320 may be any electronic device able to detect the presence or absence of a lens or other structure. For instance, it may be an absolute position sensor, a displacement sensor, a linear position sensor, axial position sensor, or a multi-axis sensor. The position sensor may use mechanical sensors, electrical sensors, or a combination of sensors.

All or part of computing subsystem 310 may operate as a component of or independent of microscope 100 or independent of any other components shown in FIGS. 1A and 1B. Computing subsystem 310 may include processor 325, memory 330 and input/output controllers 335 communicatively coupled by bus 340. Processor 325 may include hardware for executing instructions, such as those making up a computer program, such as application 345. As an example and not by way of limitation, to execute instructions, processor 325 may retrieve (or fetch) the instructions from an internal register, an internal cache, and/or memory 330; decode and execute them; and then write one or more results to an internal register, an internal cache, and/or memory 330. This disclosure contemplates processor 325 including any suitable number of any suitable internal registers, where appropriate. Where appropriate, processor 325 may include one or more arithmetic logic units (ALUs); be a multi-core processor; or include one or more processors 325. Although this disclosure describes and illustrates a particular processor, this disclosure contemplates any suitable processor.

Processor 325 may execute instructions, for example, to reconfigure a reconfigurable surgical microscope 100. For example, processor 325 may run application 345 by executing or interpreting software, scripts, programs, functions, executables, or other modules contained in application 345. Processor 325 may perform one or more operations related to FIG. 4. Input data received by processor 325 or output data generated by processor 325 may include lens position data 350.

Memory 330 may include, for example, random access memory (RAM), a storage device (e.g., a writable read-only memory (ROM) or others), a hard disk, a solid state storage device, or another type of storage medium. Computing subsystem 310 may be preprogrammed or it may be programmed (and reprogrammed) by loading a program from another source (e.g., from a CD-ROM, from another computer device through a data network, or in another manner). Input/output controller 335 may be coupled to input/output devices (e.g., monitor 355, actuators 315, position sensors 320, a mouse, a keyboard, or other input/output devices) and to communication link 365. The input/output devices may receive and transmit data in analog or digital form over communication link 365.

Memory 330 may store instructions (e.g., computer code) associated with an operating system, computer applications, and other resources. Memory 330 may also store application data and data objects that may be interpreted by one or more applications or virtual machines running on computing subsystem 310. For example, lens position data 350 and applications 345 may be stored in memory 330. In some implementations, a memory of a computing device may include additional or different data, applications, models, or other information.

Lens position data 350 may include information related to position data captured by position sensors 320 that may be used to determine if a reconfigurable objective lens 108 is positioned correctly.

Applications 345 may include software applications, scripts, programs, functions, executables, or other modules that may be interpreted or executed by processor 325. Applications 345 may include machine-readable instructions for performing one or more operations related to FIG. 4. Applications 345 may include machine-readable instructions for calculating when the reconfigurable objective lens is correctly positioned within the reconfigurable microscope. For example, applications 345 may be configured to analyze lens position data 350 to determine when the reconfigurable objective lens has been fully removed from the microscope or fully inserted within either a first or second position within the microscope. Applications 345 may generate output data and store output data in memory 330, in another local medium, or in one or more remote devices (e.g., by sending output data via communication link 365).

Communication link 365 may include any type of communication channel, connector, data communication network, or other link. For example, communication link 365 may include a wireless or a wired network, a Local Area Network (LAN), a Wide Area Network (WAN), a private network, a public network (such as the Internet), a wireless network, a network that includes a satellite link, a serial link, a wireless link (e.g., infrared, radio frequency, or others), a parallel link, or another type of data communication network.

Processor 325 may command actuators 315 to move the reconfigurable objective lens, such as reconfigurable objective lenses 108 in FIG. 1A and FIG. 1B, into and out of a first and second position. While actuator 315 is changing the positions of the reconfigurable objective lens, position sensors 320 may record position data for the reconfigurable objective lenses. Processor 325 may then execute application 345 to determine when the reconfigurable objective lens has been fully repositioned and when the reconfigurable microscope has been fully reconfigured. Processor 325 may then command actuator 315 to stop moving the reconfigurable objective lenses 108 in the desired positions. Processor 325 may also command actuators 315 to select a reconfigurable objective lens from a lens array 360. Lens array 360 may contain a number of reconfigurable objective lenses with various optical parameters. Processor 325 may then command actuators 315 to reconfigure reconfigurable microscope using one or more reconfigurable objective lenses as described above with respect to FIGS. 1A and 1B. Processor 325 may also execute application 345 to determine whether reconfigurable objective lens 108 is properly aligned in the desired position. If processor 325 or application 345 determines that reconfigurable objective lens is misaligned, a warning may be transmitted to monitor 355 and may be displayed to the user.

Figure 4:
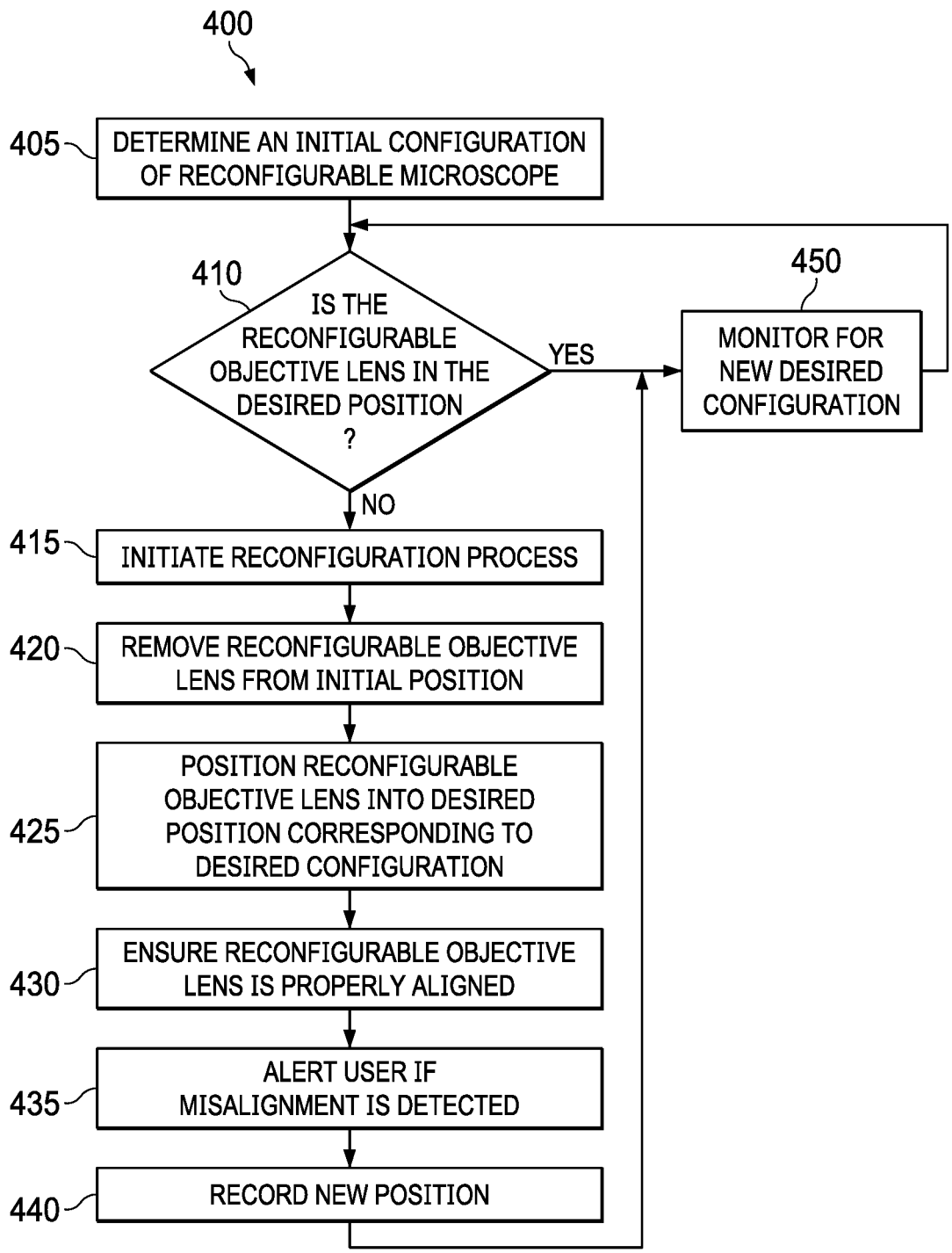
FIG. 4 is a flow chart of a method of configuring a reconfigurable surgical microscope.

FIG. 4 is a flow chart of a method of configuring a reconfigurable surgical microscope, such as reconfigurable surgical microscope 100 shown in FIGS. 1A and 1B. The steps of method 400 may be performed by a person, various computer programs, models or any combination thereof, configured to control and analyze information from microscope systems, apparatuses and devices. The programs and models may include instructions stored on a computer readable medium and operable to perform, when executed, one or more of the steps described below. The computer readable media may include any system, apparatus or device configured to store and retrieve programs or instructions such as a hard disk drive, a compact disc, flash memory or any other suitable device. The programs and models may be configured to direct a processor or other suitable unit to retrieve and execute the instructions from the computer readable media. For example, the programs and models may be one of the applications in applications 345 shown in FIG. 3. For illustrative purposes, method 400 is described with respect to microscope similar to microscope 100 illustrated in FIGS. 1A and 1B; however, method 400 may be used to reconfigure any reconfigurable surgical microscope.

Method 400 may begin at step 405 where a user of a reconfigurable microscope may determine an initial configuration of the reconfigurable microscope. The user may be able to determine the initial configuration through observation of the reconfigurable microscope. For example, the user may be able to inspect the microscope physically to determine the initial configuration. This initial configuration may include the reconfigurable microscope having a reconfigurable objective lens positioned such that the reconfigurable microscope may be said to be in either Cataract Mode or Vitreoretinal Mode.

Step 405 may also be performed by an automated configuration system. The automated configuration system may make this determination by processing sensor information received from one or more position sensors that are associated with the position of the reconfigurable objective lens of the reconfigurable microscope. For example, a position sensor associated with a first position of the reconfigurable objective lens may sense the presence of a reconfigurable objective lens in the first position. This information may then be processed by an automated configuration system and may indicate that the reconfigurable microscope is initially in Cataract Mode. For further example, a position sensor associated with a second position of the reconfigurable objective lens may sense the presence of the reconfigurable objective lens in the second position. This information may then be processed by an automated configuration system and indicate that the reconfigurable microscope is initially in Vitreoretinal Mode. Automated configuration system may also be configured to received information from both a position sensor associated with the first position and a position sensor associated with the second position. The automated configuration system may then process the information to determine the initial configuration of the reconfigurable microscope.

At step 410, a user or an automated configuration system may determine whether the reconfigurable objective lens is in a desired position that may correspond to a desired configuration of the reconfigurable microscope. Based on the initial configuration that was determined in step 405, either the user or an automated configuration system may compare the desired configuration with the initial configuration to determine whether reconfiguration is necessary. If the reconfigurable objective lens is not in the desired position, a user or an automated configuration system may proceed to step 415. If the reconfigurable objective lens is in the desired position, a user or an automated configuration system may proceed to step 450.

At step 415, a user or an automated configuration system may initiate a reconfiguration process if the initial configuration is not the desired configuration for the current application of the reconfigurable microscope. For example, if the reconfigurable microscope is initially in Cataract Mode and the user intends to use the reconfigurable microscope for a vitreoretinal surgery, then the user may initiate the reconfiguration process such that the reconfigurable microscope may be configured into Vitreoretinal Mode. For further example, the automated configuration system may sense that the reconfigurable microscope is initially in Cataract Mode but the user has indicated that the reconfigurable microscope will be used for vitreoretinal surgery. The automated configuration system may initiate the reconfiguration process such that the reconfigurable microscope may be configured into Vitreoretinal Mode.

At step 420, the user or an automated configuration system may remove the reconfigurable objective lens from an initial position. This initial position may be either the first objective lens position or the second objective lens position.

At step 425, the user or an automated configuration system may position the reconfigurable objective lens into a desired position. This desired position may be either the first position or the second position.

At step 430, the user or an automated configuration system ensures that the reconfigurable objective lens is properly removed from the initial position and properly aligned within the desired position. When the reconfigurable objective lens is removed from the initial position, it is important to ensure that the reconfigurable objective lens is fully removed from the initial position. If the lens is only partially removed, the lens or the opto-mechanical housing of the lens may interfere with or obstruct the field of view of the reconfigurable microscope and may also interfere with the illumination provided by the illumination unit when the lens if being removed from the second objective lens position. The user may remove the reconfigurable objective lens manually and may also ensure that the reconfigurable objective lens is fully removed. The automated configuration system may remove the reconfigurable objective lens by executing a software application that analyzes information from the position sensors to detect the reconfigurable objective lens, activates actuators to manipulate the reconfigurable objective lens, and then fully removes the reconfigurable objective lens ensuring full removal by further analyzing information from the position sensors to detect clearance of the reconfigurable objective lens from the initial position.

When the reconfigurable objective lens is positioned within the desired position, the user or the automated configuration system may ensure that the reconfigurable objective lens is properly aligned within the desired position. If the reconfigurable objective lens is improperly aligned, the same issues as discussed above with reference to only partially removing the reconfigurable objective lens from the initial position may result. The user may position the reconfigurable objective lens manually and may also ensure that the reconfigurable objective lens is properly aligned. The automated configuration system may position the reconfigurable objective lens by executing a software program that activates actuators to manipulate the reconfigurable objective lens, positions the reconfigurable objective lens within the desired position, and then ensures that the reconfigurable objective lens is properly aligned within the desired position by analyzing information from the position sensors to detect the position and alignment of the reconfigurable objective lens.

At step 435, the automated configuration system may alert the user of the misalignment or failed removal of the reconfigurable objective lens. The automated configuration system may alert the user using various methods. For example, automated configuration system may initiate a flashing light, may display text including the alert on a display, and/or may generate an audible alarm. Other methods of alerting the user may also be used.

At step 440, the user or an automated configuration system may record the new position. This new position may correspond to an initial configuration of the reconfigurable microscope that may be used at step 405. This new position may also be compared with a new desired configuration at step 450.

At step 450, a user or an automated configuration system may monitor the reconfigurable microscope until a new desired configuration arises. If the reconfigurable objective lens is in an initial position that corresponds to a desired position, a user or an automated configuration system will continue to monitor for a new desired configuration. Following completion of steps 410 through 440, when the reconfigurable microscope is reconfigured, a user or an automated configuration system will also monitor for a new desired configuration.

Modifications, additions, or omissions may be made to method 400 without departing from the scope of the present disclosure. For example, the order of the steps may be performed in a different manner than that described and some steps may be performed at the same time. Additionally, each individual step may include additional steps without departing from the scope of the present disclosure.

The invention claimed is:

1. An automated surgical microscope configuration system, comprising:
    a processor;
    a position sensor coupled to the processor;
    a reconfigurable surgical microscope coupled to the position sensor, the reconfigurable surgical microscope including:
        an eyepiece;
        a relay lens system optically coupled to the eyepiece;
        a zoom lens system optically coupled to the eyepiece and the relay lens system;
        an illumination unit; and
        a reconfigurable objective lens capable of being repositioned between a first objective lens position and a second objective lens position, the first objective lens position comprising a first slot located between the zoom lens system and the illumination unit and the second objective lens position comprising a second slot located such that the illumination unit is located between the second objective lens position and the zoom lens system; and
    an actuator coupled to the processor and the reconfigurable objective lens and configured to move the reconfigurable objective lens into either the first lens position or the second lens position.

2. The automated surgical microscope configuration system of claim 1, wherein the reconfigurable objective lens comprises multiple movable lenses.

3. The automated surgical microscope configuration system of claim 1, wherein the position sensor comprises multiple position sensors associated with at least one of the first objective lens position or the second objective lens position.

4. The automated surgical microscope configuration system of claim 1, wherein the actuator comprises multiple actuators.

* * * * *